US011298327B2

United States Patent
Sun et al.

(10) Patent No.: US 11,298,327 B2
(45) Date of Patent: Apr. 12, 2022

(54) METHODS AND COMPOSITIONS FOR TREATING AND PREVENTING ARTHRITIS

(71) Applicant: Albert Einstein College of Medicine, Bronx, NY (US)

(72) Inventors: Hui B. Sun, Chappaqua, NY (US); Daniel J. Leong, Forest Hills, NY (US); Neil J. Cobelli, Scarsdale, NY (US); David M. Hirsh, Scarsdale, NY (US); John A. Hardin, New York, NY (US); Karen E. Sperling, New Rochelle, NY (US); Sun J. Kim, New York, NY (US); David C. Spray, Pelham, NY (US); Chandan Guha, Scarsdale, NY (US); Marwa Choudhury, Bronx, NY (US)

(73) Assignee: Albert Einstein College of Medicine, Bronx, NY (US)

( * ) Notice: Subject to any disclaimer, the term of this patent is extended or adjusted under 35 U.S.C. 154(b) by 0 days.

(21) Appl. No.: 17/017,999

(22) Filed: Sep. 11, 2020

(65) Prior Publication Data
US 2020/0405661 A1 Dec. 31, 2020

Related U.S. Application Data

(62) Division of application No. 15/520,156, filed as application No. PCT/US2015/058544 on Nov. 2, 2015, now Pat. No. 10,772,846.
(Continued)

(51) Int. Cl.
*A61K 31/05* (2006.01)
*A61K 9/00* (2006.01)
(Continued)

(52) U.S. Cl.
CPC ............ *A61K 31/05* (2013.01); *A61K 9/0014* (2013.01); *A61K 9/0019* (2013.01);
(Continued)

(58) Field of Classification Search
None
See application file for complete search history.

(56) References Cited

U.S. PATENT DOCUMENTS

2006/0172012 A1 8/2006 Finley et al.
2007/0014883 A1 1/2007 Rohdewald
(Continued)

FOREIGN PATENT DOCUMENTS

WO 2010019034 A1 2/2010
WO 2014023952 A2 2/2014

OTHER PUBLICATIONS

Yokota et al., " CITED2—mediated Regulation of MMP-1 and MMP-13 in Human Chondrocytes under Flow Shear", The Journal of Biological Chemistry, vol. 278, 2003, No. 47, pp. 47275-47280. (Year: 2003).*
(Continued)

*Primary Examiner* — Kyung S Chang
(74) *Attorney, Agent, or Firm* — Fox Rothschild LLP

(57) ABSTRACT

Methods and formulations are provided for treating or preventing arthritis, in particular osteoarthritis, where the formulation to be administered to a subject for treating or preventing arthritis comprises carvacrol, curcumin, epigallocatechin-3-gallate and oligomeric procyanidins.

16 Claims, 6 Drawing Sheets

Related U.S. Application Data

(60) Provisional application No. 62/076,842, filed on Nov. 7, 2014.

(51) Int. Cl.
*A61K 31/12* (2006.01)
*A61K 31/353* (2006.01)
*A61P 19/02* (2006.01)

(52) U.S. Cl.
CPC ............ *A61K 9/0053* (2013.01); *A61K 31/12* (2013.01); *A61K 31/353* (2013.01); *A61P 19/02* (2018.01)

(56) References Cited

U.S. PATENT DOCUMENTS

2014/0099390 A1    4/2014  Antony
2015/0258094 A1*   9/2015  Chen .................... A61K 9/0092
                                                        424/9.6

OTHER PUBLICATIONS

PCT International Search Report and Written Opinion dated Jan. 27, 2016 for PCT International Patent Application No. PCT/US2015/058544, 9 pages.

Li, "Can oil of Oregano Help with Arthritis?", EzineArticles, pp. 1-2, 2012 (Year: 2012).

Jackson et al., "The antioxidants curcumin and quercetin inhibit inflammatory processes associated with arthritis", Inflammation Research, Apr. 2006, vol. 55, Issue 4, pp. 168-175. (Year: 2006).

Singh et al., "Green tea polyphenol epigallocatechin-3-gallate: inflammation and arthritis", Life Sci. Jul. 30, 2010; 87(5-6) 196 (Year: 2010).

Miyake et al., "Oral administration of highly oligomeric procyanidins (HOPC) of Jatoba reduces the severity of collagen-induced arthritis", Biosci Biotechnol Biochem, Jul. 2008, 72(7): 1781-8 (Year: 2008).

\* cited by examiner

METHODS AND COMPOSITIONS FOR TREATING AND PREVENTING ARTHRITIS

CROSS-REFERENCE TO RELATED APPLICATIONS

This application is a divisional of U.S. patent application Ser. No. 15/520,156, filed Apr. 19, 2017, which is a U.S. national stage entry under 35 U.S.C. § 371 of PCT International Patent Application No. PCT/US2015/058544, filed Nov. 2, 2015, which claims the benefit of U.S. Provisional Patent Application No. 62/076,842, filed Nov. 7, 2014, the contents of each of which are incorporated by reference.

STATEMENT OF GOVERNMENT SUPPORT

This invention was made with government support under grant number AR050968 awarded by the National Institutes of Health. The government has certain rights in the invention.

BACKGROUND OF THE INVENTION

Throughout this application various publications are referred to in parentheses. Full citations for these references may be found at the end of the specification before the claims. The disclosures of these publications are hereby incorporated by reference in their entireties into the subject application to more fully describe the art to which the subject application pertains.

Arthritis is a leading cause of pain and disability. Osteoarthritis (OA) affects over 27 million Americans (1,2) and is a great economic burden in the United States with over $185.5 billion in annual medical care expenditures (3-7). The number of subjects suffering from arthritis is expected to grow to over 67 million by 2030. The growth is credited to an increased aging population and increased prevalence of obesity. Within this population, 29.8% of the 45-64 age group report doctor-diagnosed arthritis and 50% of persons aged 65 or older are diagnosed with osteoarthritis. While 16.4% of under/normal weight adults report doctor-diagnosed arthritis, 52.5% of arthritis patients are overweight or obese. Furthermore, patients who suffered from joint injury currently account for 12% of all OA cases, which is approximately 5.6 million in the United States.

Several treatments are available for osteoarthritis, including physical therapy, pharmacological therapies such as glucosamine sulfate, chondroitin sulfate, non-steroidal anti-inflammatory drugs (NSAIDs), corticosteroids, weak opioids or other analgesics, and finally end-stage disease management and surgery (8). However, there is currently no cure for osteoarthritis nor do current therapies effectively slow or arrest its progression (5,9). Moreover, many of the pharmacological agents used to treat osteoarthritis are associated with detrimental gastrointestinal, renal, and cardiovascular side effects with long term use (10-12). There are also many nutraceutical-based compounds (e.g. turmeric/curcumin, green tea, glucosamine, hyaluronic acid) marketed to treat joint pain and arthritis, but their effectiveness in treating OA have not been clearly demonstrated, and none of these supplements have been approved by the FDA to treat or cure disease (13). While current therapeutic approaches may relieve pain and some disease symptoms, they may fail to prevent or slow the progression of osteoarthritis because they do not adequately correct the pathological alterations in specific cellular and molecular pathways that are responsible for the disease.

The present invention addresses the need for improved treatments for arthritis, such as osteoarthritis and rheumatoid arthritis, where the treatments are safe, effective and suitable for decades-long treatment.

SUMMARY OF THE INVENTION

The invention provides methods of treating or preventing arthritis, such as osteoarthritis, in a subject in need thereof comprising administering to the subject a formulation or composition comprising carvacrol, curcumin, epigallocatechin-3-gallate and oligomeric procyanidins in an amount effective to treat or prevent arthritis.

The invention also provides formulations or compositions for treatment or prevention of arthritis comprising carvacrol, curcumin, epigallocatechin-3-gallate and oligomeric procyanidins, and a pharmaceutically acceptable carrier.

This invention is superior to existing technologies because it arrests the development of osteoarthritis, which no product currently on the market can claim.

DETAILED DESCRIPTION OF THE INVENTION

Figure 1:
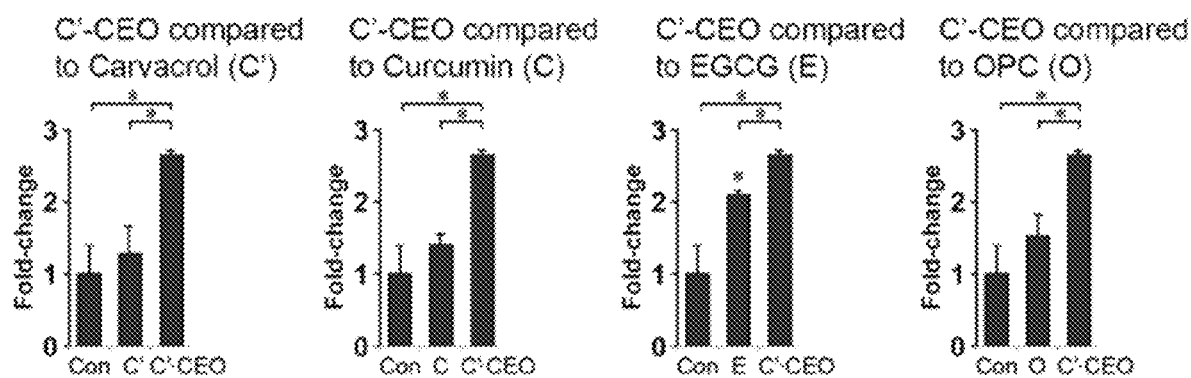
FIG. 1. The C'-CEO formulation (combination of carvacrol, curcumin, epigallocatechin-3-gallate and oligomeric procyanidins) exerted highest efficacy in increasing expression of CITED2, a novel cartilage/chondrocyte protection molecular target, in comparison to the individual components of C'-CEO. Human chondrocytes (C28/I2) treated with Carvacrol (C', 1 µM), Curcumin (C, 1 µM), EGCG (E, 100 µM), OPC (O, 50 µg/ml), or C'-CEO for 3 hours in the presence of IL-1β (10 ng/µl) were analyzed by real-time PCR. Bars represent mean CITED2 expression±SEM. $*p<0.05$ using one-way ANOVA with Tukey post-hoc test compared to control or indicated comparison), n=6/group.
Figure 2A:
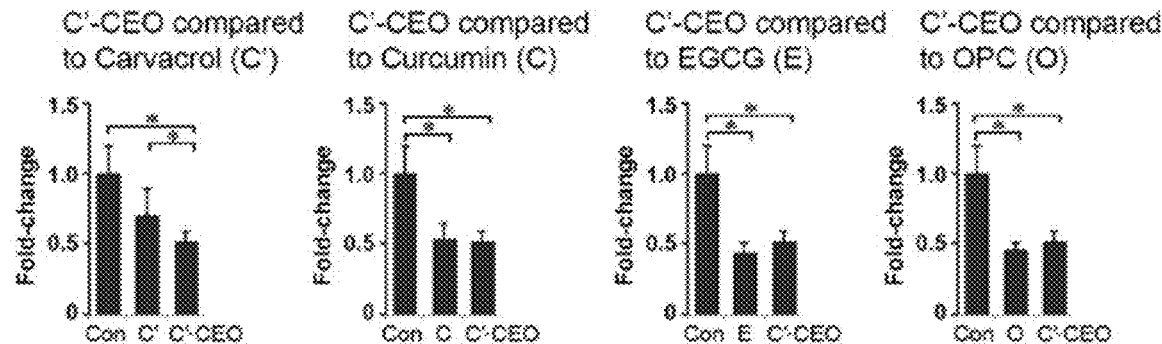
FIG. 2A-2E. C'-CEO exerts the highest efficacy in suppressing expression of cartilage degradation enzymes MMP-1 (A), MMP-3 (B), MMP-13 (C), ADAMTS5 (D) and pro-inflammatory mediator TNF-α (E), in comparison to the individual components of C'-CEO. Human chondrocytes (C28/I2) treated with Carvacrol (C', 1 µM), Curcumin (C, 1 µM), EGCG (E, 100 µM), OPC (O, 50 µg/ml), or C'-CEO (combination of all compounds) for 3 hours in the presence of IL-1β (10 ng/µl), a cell culture model of osteoarthritis. Data were analyzed by real-time PCR. Bars represent mean gene expression of MMP-1, -3, -13, ADAMTS5, TNF-α±SEM. $*p<0.05$ using one-way ANOVA with Tukey post-hoc test compared to control or indicated comparison, n=6/group.
Figure 2B:
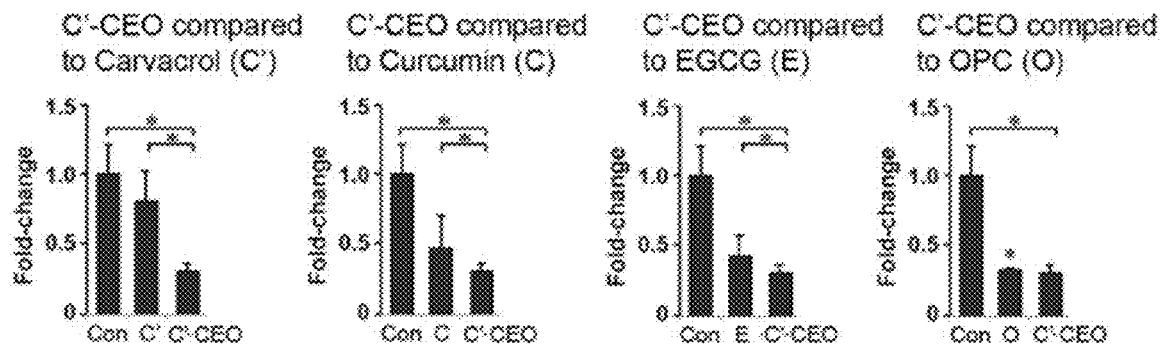
Figure 2C:
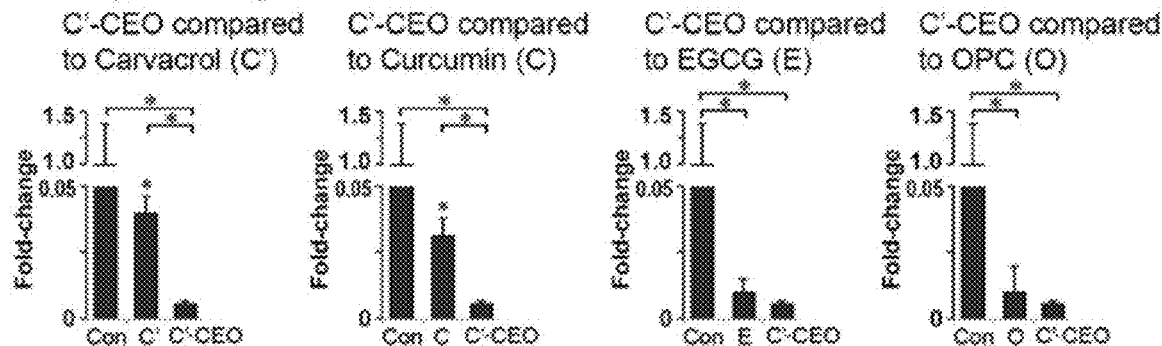
Figure 2D:
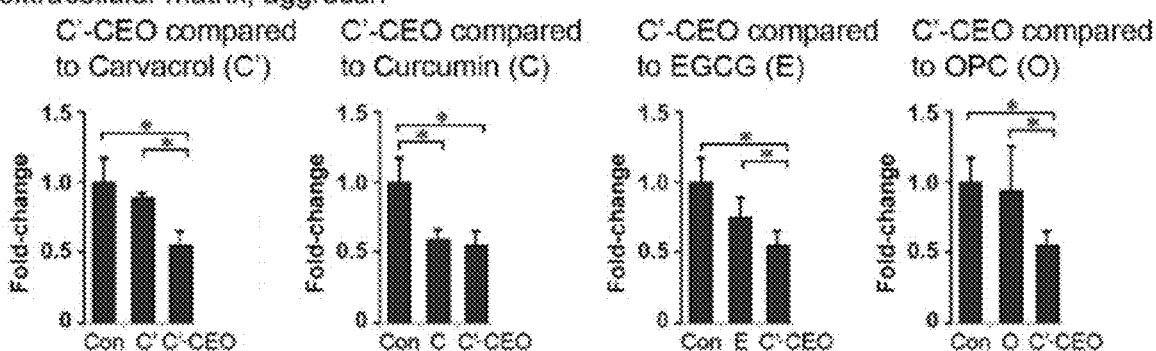
Figure 2E:
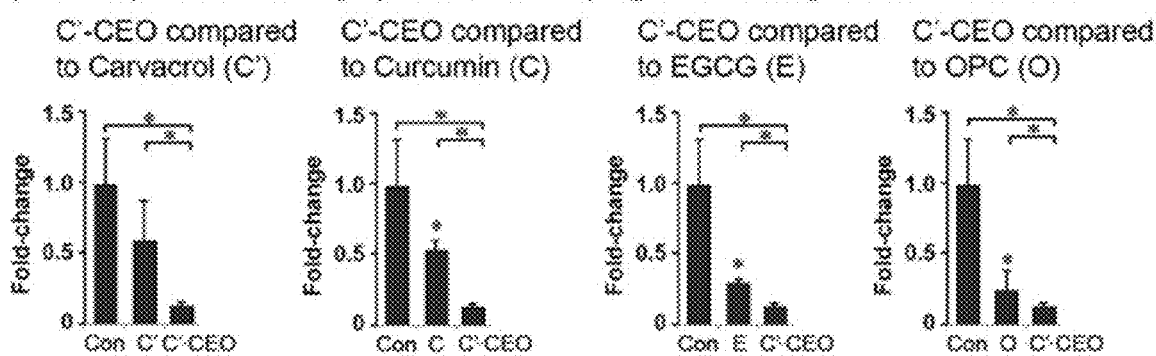

The invention provides a method of treating or preventing arthritis in a subject in need thereof comprising administering to the subject a formulation or composition comprising carvacrol, curcumin, epigallocatechin-3-gallate and oligomeric procyanidins in an amount effective to treat or prevent arthritis.

The arthritis can be, for example, osteoarthritis, which can arise for example subsequent to injury to a joint. In another embodiment, the arthritis can be, for example, rheumatoid arthritis.

As used herein, to "treat" arthritis means to ameliorate a sign and/or symptom of arthritis and/or to arrest the development of arthritis. Preferably, administration of the formulation or composition to the subject arrests or slows the breakdown of joint tissue affected by arthritis. Preferably, administration of the formulation or composition to the subject reduces inflammation associated with arthritis. Preferably, administration of the formulation or composition to the subject relieves painful symptoms of arthritis. Preferably, administration of the formulation or composition to the subject improves one or more of sensitivity to mechanical stimuli, joint movement and joint function.

To "prevent" arthritis means to prevent the development of arthritis in a subject at risk for development of arthritis. In one embodiment, for example, the subject has sustained a joint injury and is taking the formulation or composition to prevent development of post-traumatic osteoarthritis.

The invention also provides a formulation or composition for treatment or prevention of arthritis comprising four nutraceuticals: Carvacrol (C'), Curcumin (C), Epigallocatechin-3-gallate (E), and Oligomeric procyanidins (O) ("C'-CEO" formulation or composition) and a pharmaceutically acceptable carrier. In one embodiment, the active ingredients of the formulation or composition consist of carvacrol, curcumin, epigallocatechin-3-gallate and oligomeric procyanidins.

As used herein, a "pharmaceutically acceptable carrier" is (i) compatible with the other ingredients of the composition without rendering the composition unsuitable for its intended purpose, and (ii) suitable for use with subjects as provided herein without undue adverse side effects (such as toxicity, irritation, and allergic response). Side effects are "undue" when their risk outweighs the benefit provided by the composition. Non-limiting examples of pharmaceutically acceptable carriers include any of the standard pharmaceutical carriers such as phosphate buffered saline solutions, water, and emulsions such as oil/water emulsions and microemulsions.

The formulation or composition can be administered to subjects using routes of administration known in the art. Preferred routes of administration include oral administration, intra-articular injection, and topical administration. One or more of the components of the C'-CEO formulation can be nano-encapsulated to improve its solubility. The C'-CEO formulation can be encapsulated in enteric-coated capsules for oral delivery to limit gastrointestinal degradation.

In one embodiment, the molar ratio of carvacrol, curcumin, EGCG and OPC in the formulation or composition is 1:1:100:50. In one embodiment, the weight ratio of carvacrol, curcumin, EGCG and OPC in the formulation or composition is 10:10:1:10.

This invention will be better understood from the Experimental Details that follow. However, one skilled in the art will readily appreciate that the specific methods and results discussed are merely illustrative of the invention as described more fully in the claims that follow thereafter.

EXPERIMENTAL DETAILS

Materials and Methods

Induction of Osteoarthritis in Mice.

All studies were approved by the Albert Einstein College of Medicine Institutional Animal Care and Use Committee. Destabilization of the medial meniscus (DMM) was established in adult C57BL/6 mice (male, 5-6 months) by surgically transecting the medial meniscotibial ligament (MMTL) in the right hind limb (36). Briefly, the joint capsule immediately medial to the patellar tendon was incised, followed by blunt dissection of the fat pad, to provide visualization of the MMTL of the medial meniscus. The MMTL was transected, leading to DMM. In the sham surgery, the MMTL was visualized but not transected. The joint capsule and skin were closed with suture.

Immunohistochemistry, Safranin O Staining, and OARSI Score Evaluation.

Animals were euthanized, hindlimbs were fixed in formalin, decalcified in formic acid, embedded in paraffin and sectioned for histology and immunohistochemistry. Sections were incubated overnight at 4° C. with antibodies against cleaved aggrecan (NITEGE, Ibex) and cleaved type II collagen (Col2-3/4M, Ibex), MMP-13 (Abcam), and ADAMTS5 (Abcam) followed by incubation with anti-mouse or anti-rabbit secondary antibody (Biocare Medical) and visualization with DAB chromagen (Vector Laboratories). Negative controls were stained with irrelevant isotype-matched antibodies (Biocare Medical). Safranin 0-fast green staining was used to visualize proteoglycans in the articular cartilage. Severity of OA was evaluated for each mouse using the Osteoarthritis Research Society International (OARSI) scoring system (34). Immunostaining intensity for type II collagen or aggrecan cleavage epitopes was quantified by determining the "reciprocal intensity" of the stained articular cartilage matrix. Briefly, the light intensity value of random locations within azones from the posterior to anterior direction of the femoral and tibial condyles was measured using the color picker in Adobe Photoshop (37). Percentages of positive MMP-13 and ADAMTS5 chondrocytes were determined by counting the number of immunostained cells and dividing by the total number of chondrocytes visualized by a hematoxylin counterstain (Vector Laboratories).

Tactile Sensitivity Testing.

Mice were acclimated for 30 minutes in individual chambers on top of a wire grid platform prior to von Frey testing. The plantar surface of the hind paw was stimulated with ascending force intensities of von Frey filaments (Stoelting) to determine tactile sensitivity. A positive response was defined as a rapid withdrawal of the hind paw when the stimulus was applied, and the number of positive responses for each stimulus was recorded. Tactile threshold was defined as a withdrawal response in 5 out of 10 trials to a given stimulus intensity (38). This threshold was calculated once per animal.

Open Field Behavioral Test.

Mice were acclimated to the test room for 30 min before open field testing. Mice were placed in the center of individual plexiglass square chambers (45 cm×45 cm) and allowed to freely explore the chamber for the duration of the test session. The movements of the mice were recorded with a video camera. Upon completion of the test, each mouse was returned to its home cage (39). Mouse movements were manually traced to calculate the distance (in cm) the mouse traveled within the cage in 6 min. The number of times each mouse reared (standing on its hind limbs) within 6 min was recorded by two observers blinded to treatment group assignments.

Results

Selection of Components of C'-CEO Formulation.

The C'-CEO formulation was identified by an innovative screening strategy; it is formulated from nutraceutical compounds that induce the expression of a chondroprotective transcriptional regulator CITED2 (Cbp/p300 Interacting Transactivator with ED-rich tail 2), a potential osteoarthritis therapeutic target (29-32). CITED2 mediates a novel pathway that plays a critical role in chondroprotection, at least in part by suppressing expression and activity of cartilage degrading enzymes MMP-13 and ADAMTS-5 (29, 31). Notably, CITED2 deficiency is associated with degradation of human osteoarthritic cartilage and post-traumatic osteoarthritic mice. Experimental reduction of CITED2 expression in synovial joint tissues causes osteoarthritis (29, 31). Gene transfer of CITED2 effectively slows post-traumatic disease initiation and progression in mice (30).

Because of the chronic nature of osteoarthritis and the need for long-term therapies, the inventors searched for activators of CITED2—a novel target for osteoarthritis treatment among non-toxic nutraceutical compounds. It was first found that green tea extract EGCG suppresses MMP-13 and ADAMTS-5 by inducing CITED2 (35). To enhance the potency of this potential drug, three other compounds were identified that synergistically enhance CITED2 induction and other anti-arthritic effects. The C'-CEO formulation is a product designed to exhibit both disease-modifying and symptom-modifying properties and to be effective for both prevention and treatment of arthritis such as osteoarthritis.

Effect of the C'-CEO Formulation on Expression of CITED2, a Novel Cartilage/Chondrocyte Protection Molecular Target.

The experiments were conducted in an in vitro OA model—chondrocyte cultured in the presence of pro-inflammatory cytokine IL-1β, which mimics OA conditions in humans. This system has been well recognized and is commonly used as validation of drug screening for OA. Human chondrocytes (C28/I2) were treated with Carvacrol (C', 1 µM), Curcumin (C, 1 µM), EGCG (E, 100 µM), OPC (O, 50 µg/ml), or C'-CEO (combination of all compounds) for 3 hours in the presence of IL-1β(10 ng/µl), a cell culture model of osteoarthritis. Data were analyzed by real-time PCR.

C'-CEO compared to each individual compound carvacrol (C'), curcumin (C), EGCG (E) and Oligomeric Proanthocyanidins (O) exerted the highest increase in expression of CITED2 (FIG. 1). The C'-CEO formulation synergistically increased expression of CITED2 to a degree higher than each individual compound alone.

Effect of C'-CEO Formulation on Expression of Proteolytic Enzymes (MMPs 1, 3, 13, ADAMTS5), and Pro-Inflammatory Mediator TNF-α, which Play Critical Roles in OA Development.

To determine the potential therapeutic efficacy of C'-CEO, the ability of the C'-CEO formulation to reduce expression of proteolytic enzymes and a pro-inflammatory cytokine was tested in vitro. Proteolytic enzymes such as matrix metalloproteinases (MMP)-1, -3, -13, and A Disintegrin And Metalloproteinase with Thrombospondin Motifs (ADAMTS5) are highly expressed in arthritic cartilage, and directly cleave the cartilage extracellular matrix. Mice with MMPs or ADAMTS knocked out have been demonstrated to be resistant to the development of OA, suggesting targeting these enzymes will have therapeutic benefit. In addition, expression of pro-inflammatory cytokines, such as IL-1β and TNF-α are increased in arthritic tissue, and upregulate expression of MMPs/ADAMTS.

Human chondrocytes (C28/I2) were treated with Carvacrol (C', 1 µM), Curcumin (C, 1 µM), EGCG (E, 100 µM), OPC (O, 50 µg/ml), or C'-CEO (combination of all compounds) for 3 hours in the presence of IL-1β (10 ng/µl), a cell culture model of osteoarthritis. Data were analyzed by real-time PCR.

Each individual compound exerted some efficacy in suppressing expression of MMP-1, 3, 13, ADAMTS5, and pro-inflammatory cytokine TNF-α. However, overall, C'-CEO was most the effective in suppressing expression of these targets, compared to each individual compound and vehicle control (FIG. 2). C'-CEO effectively suppressed expression of multiple cartilage degradative enzymes and a pro-inflammatory mediator, suggesting it has therapeutic potential for treating OA.

Efficacy of C'-CEO Formulation In Vivo in Slowing Progression of OA.

To determine the efficacy of the C'-CEO formulation in slowing progression of OA in vivo, a well-established post-traumatic mouse model of OA was used. These OA mice were orally administered C'-CEO, individual compounds, or placebo daily. Severity of OA was evaluated 8 weeks after induction of OA, using a well-established and FDA recommended cartilage integrity stain, Safranin O, and a semi-quantitative Osteoarthritis Research Society International (OARSI) scoring system. Furthermore, the efficacy of the C'-CEO formulation was validated by examining the level of breakdown of two major cartilage matrix proteins, type II collagen and aggrecan, as cartilage degradation is a hallmark of OA. It was further examined how the C'-CEO formulation may have such effect by targeting CITED2 by examining CITED2 expression in the articular cartilage of these OA mice.

Since as described above, the C'-CEO formulation was more effective than its individual components in increasing expression of CITED2 and in suppressing expression of major proteolytic enzymes and a pro-inflammatory mediator involved in OA initiation and development, the efficacy of the C'-CEO formulation was determined in slowing progression of OA in a post-traumatic OA mouse model.

All studies were approved by the Albert Einstein College of Medicine Institutional Animal Care and Use Committee. Destabilization of the medial meniscus (DMM) was established in adult C57BL/6 mice (male, 5-6 months) by surgically transecting the medial meniscotibial ligament (MMTL) in the right hind limb. Immediately after surgery, mice were administered either carvacrol (C'), curcumin (C), EGCG (E), OPC (O), C'-CEO, or vehicle control for 8 weeks. At 8 weeks following surgery, animals were euthanized, the hindlimbs were fixed in formalin, decalcified in formic acid, embedded in paraffin and sectioned for histology. Safranin O, a well-established cartilage stain, was used to visualize integrity of the articular cartilage and aggrecans in the articular cartilage. Severity of OA was evaluated using the OARSI scoring system.

Figure 3:
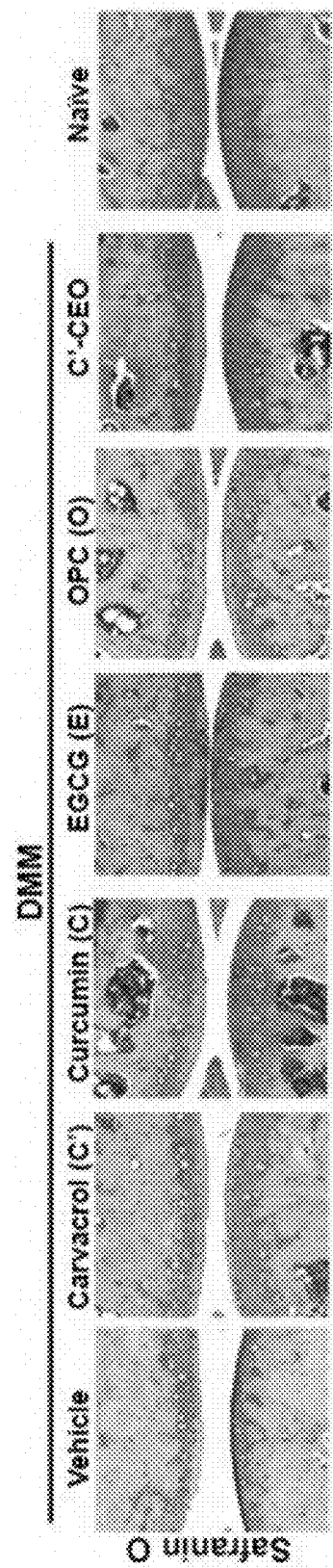
FIG. 3. Mice treated with C'-CEO formulation exhibited the least amount of histologic cartilage damage compared to individual components of C'-CEO. Carvacrol (C': 50 mg/kg), Curcumin (C: 50 mg/kg), EGCG (E: 5 mg/kg), OPC (O: 50 mg/kg), C'-CEO (combination of all compounds) or vehicle were administered daily (7 days/week) for 8 weeks via oral gavage in DMM mice (C57BL/6, male, 6 mo., n=8/group), with naïve as an additional control. OA severity based on Safranin 0 staining.

While the individual compounds—carvacrol (C'), curcumin (C), EGCG (E), and OPC (O), exhibited some reduction in cartilage degradation, mice fed the C'-CEO formulation exhibited the least amount of cartilage damage (fibrillation, erosion, loss of aggrecans), as determined histologically with Safranin O staining (FIG. 3). The cartilage of C'-CEO mice also exhibited quantitatively the lowest OA score, established by an OA scoring system (OARSI score), compared to treatment with each individual compound alone (Table 1). Thus, while treatment with the individual compounds exerted some efficacy in cartilage protection, treatment with the combination of all four nutraceuticals, the C'-CEO formulation, exerted the greatest efficacy in slowing progression of OA in a post-traumatic OA animal model.

Efficacy of C'-CEO Formulation on Preventing the Breakdown of the Cartilage Extracellular Matrix, a Hallmark of OA, and in Increasing CITED2 Expression In Vivo.

The cartilage extracellular matrix consists primarily of two proteins: type II collagen and aggrecan. Breakdown of these matrix proteins is a hallmark of OA. Therefore, the efficacy of the C'-CEO formulation on preventing breakdown of these proteins, and also its effect on the expression of CITED2, the molecular target of C'-CEO, were examined.

Figures 4A, 4B:
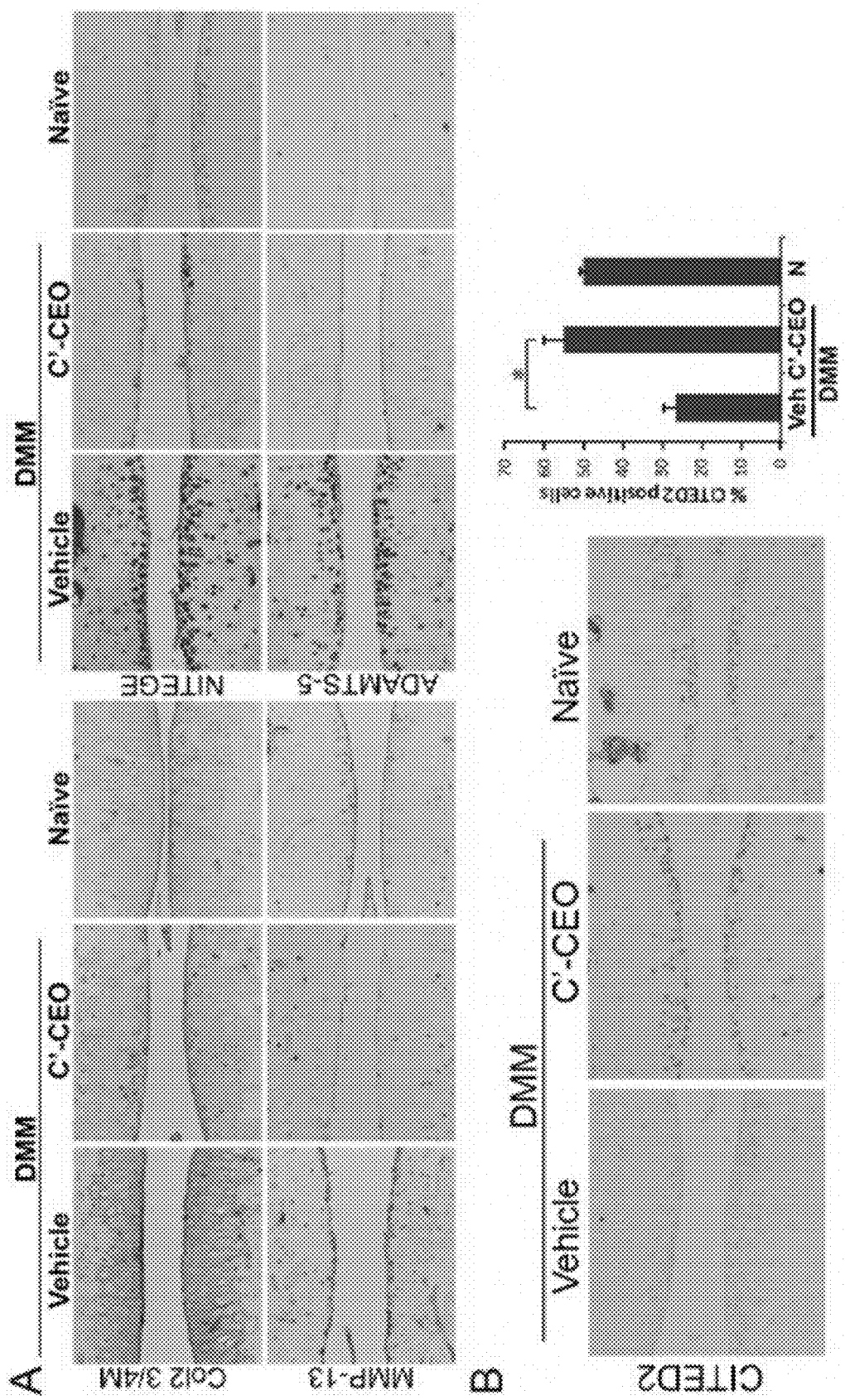
FIG. 4A-4B. The C'-CEO formulation prevents breakdown of the cartilage extracellular matrix, suppresses proteolytic enzymes MMP-13 and ADAMTS5, and increases expression of CITED2 in an OA mouse model. A. Immunohistochemistry for denatured type II collagen (Col2 3/4M), cleaved aggrecan (NITEGE), MMP-13 and ADAMTS-5 in the articular cartilage of vehicle or C'-CEO-treated DMM mice and naïve controls. B. Immunohistochemistry for CITED2 and % of CITED2 positive chondrocytes in the articular cartilage of vehicle or C'-CEO-treated DMM mice and naïve controls.

The articular cartilage of C'-CEO-treated mice exhibited less positive immunostaining for cleaved type II collagen (Col2 3/4M) and cleaved aggrecan (NITEGE), when compared to vehicle-treated mice. The number of chondrocytes expressing MMP-13 and ADAMTS5, which cleave type II collagen and aggrecan, respectively, was also examined. C'-CEO-treated mice had fewer chondrocytes expressing MMP-13 and ADAMTS in the articular cartilage, when compared to vehicle controls (FIG. 4A). Tissue sections from the hind limbs of experimental animals were incubated overnight at 4° C. with antibodies against cleaved aggrecan (NITEGE, Ibex) and type II collagen (Col2-3/4M, Ibex), MMP-13 (Abcam), and ADAMTS5 (Abcam) followed by incubation with anti-mouse or anti-rabbit secondary antibody (Biocare Medical) and visualization with DAB chromagen (Vector Laboratories). Negative controls were stained with irrelevant isotype-matched antibodies. C'-CEO-treated mice also contained a higher percentage of chondrocytes expressing CITED2 (FIG. 4B). The C'-CEO formulation may exert efficacy in cartilage protection by slowing degradation of the two main cartilage extracellular matrix proteins (type II collagen and aggrecan), and upregulating CITED2 in the articular cartilage.

Efficacy of the C'-CEO Formulation in Relieving OA-Related Pain in a Well-Established Post-Traumatic OA Animal Model.

The progression of OA is accompanied by secondary clinical symptoms, most prominently pain. In addition to evaluating the disease-modifying effect of the C'-CEO formulation, it was determined whether C'-CEO exerted pain relief in this OA animal model, at 8 weeks following OA induction. To determine pain relief, three animal behavior assessments were used: 1) von Frey, which determined sensitivity to mechanical stimuli [OA animals tend to have lower thresholds of pain to mechanical stimuli]; 2) distance traveled—a measure of joint movement [OA animals tend to move a lesser distance compared to non-OA animals]; 3) rearing—a measure of joint function [OA animals tend to rear, or stand up on their hind limbs less than non-OA animals].

Figure 5A:
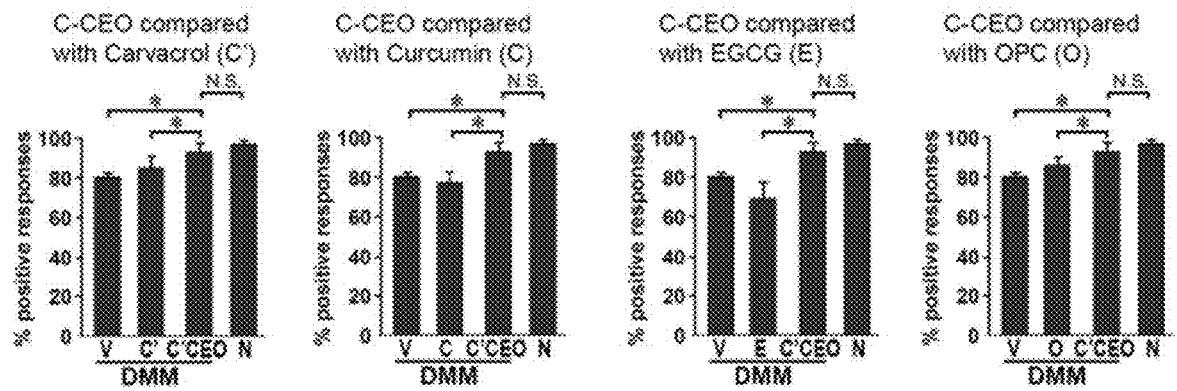
FIG. 5A-5C. C'-CEO exerted the greatest effect on pain relief using well-established pain assessments in a post-traumatic OA animal model. Arthritic pain was assessed in DMM OA mice treated as described in FIG. 3. At 8 weeks after DMM, OA-associated pain was assessed using assays of (A) von Frey (mechanical allodynia), and (B) distance traveled and (C) hind limb rearing. The von Frey test consisted of exposing the hind paw to von Frey filaments in ascending order. Groups were evaluated using number of withdrawal responses normalized to their baseline. The open field behavioral test measured the distance (cm) traveled and times reared (standing on hind limbs) in 6 min. Bars represent mean values±SEM. *$p<0.05$ using one-way ANOVA with Tukey post-hoc test compared to control or indicated comparison, n=8/group.
Figure 5B:
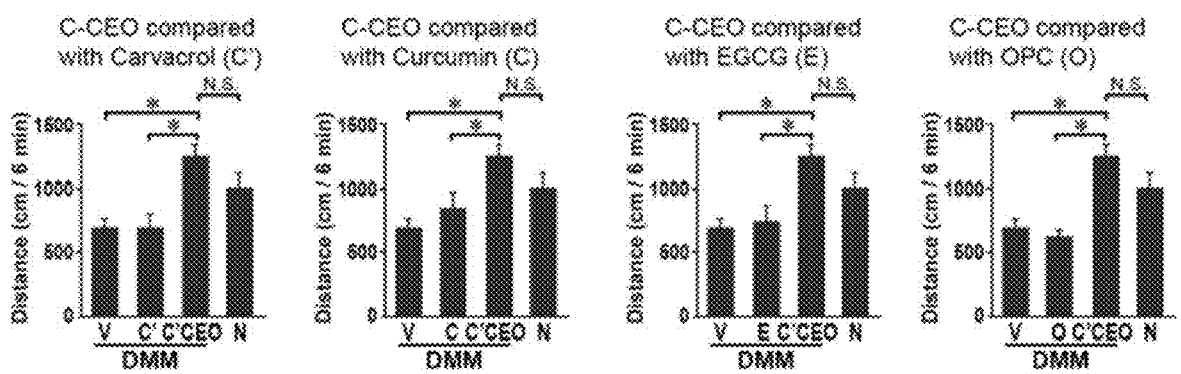
Figure 5C:
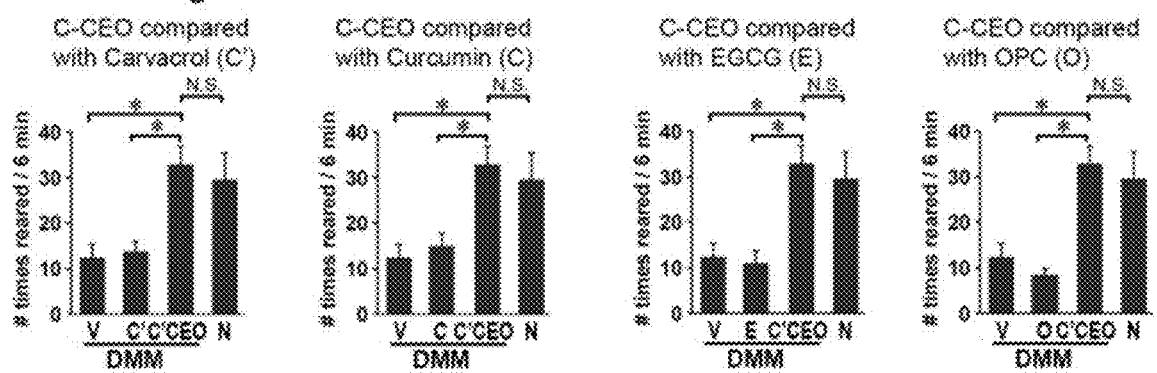

Treatment with the individual compounds, compared to the vehicle control did not improve sensitivity of the mice to mechanical stimuli (FIG. 5A), did not increase distance traveled (FIG. 5B), and did not increase hind limb rearing (FIG. 5C). In contrast, C'-CEO-treated DMM mice, like naïve controls, required a higher force to elicit paw withdrawal ($p<0.05$, FIG. 5A), traveled a longer distance ($p<0.05$, FIG. 5B), and increased rearing/standing on their hind limbs ($p<0.05$, FIG. 5C).

Treatment through oral administration with the individual compounds of carvacrol, curcumin, EGCG, or OPC did not result in a statistical improvement in pain relief of OA-associated pain. However, C'-CEO-treated OA mice exhibited statistical improvements in pain relief, with levels of mechanical sensitivity, joint movement and function, on levels similar to naïve, non-OA animals.

TABLE 1

Mice treated with C'-CEO formulation exhibited the lowest OA histologic score. OARSI score is a semi-quantitative histologic-based scoring system with 0 indicating healthy cartilage and 6 representing severe cartilage erosion. The mean OARSI score of 8 animals/group is presented ± standard deviation.

| C'-CEO vs. Carvacrol (C') | |
|---|---|
| Vehicle | 4 ± 0.5 |
| Carvacrol | 2.9 ± 0.45* |
| C'-CEO | 1.75 ± 0.24** |
| C'-CEO vs. Curcumin (C) | |
| Vehicle | 4 ± 0.5 |
| Curcumin | 2.4 ± 0.42* |
| C'-CEO | 1.75 ± 0.24** |
| C'-CEO vs. EGCG (E) | |
| Vehicle | 4 ± 0.5 |
| EGCG | 2.1 ± 0.29* |
| C'-CEO | 1.75 ± 0.24** |
| C'-CEO vs. OPC (O) | |
| Vehicle | 4 ± 0.5 |
| OPC | 2.3 ± 0.32* |
| C'-CEO | 1.75 ± 0.24** |

*$p < 0.05$, one-way ANOVA compared to vehicle-treated animals.
** $p < 10.05$, one-way ANOVA compared to individual-treatments.

DISCUSSION

The present results provide clear evidence that in vivo the invented C'-CEO formulation exerts statistically significant synergistic effects not only on osteoarthritis disease initiation and progression, but also on relieving pain symptoms and improving mobility, when compared to each individual treatment alone and to vehicle controls. The C'-CEO formulation significantly slowed development of post-traumatic osteoarthritis when oral administration was begun immediately after DMM injury in mice. Preventing or reducing the severity of osteoarthritis is extremely valuable because tissue damage is very difficult to reverse. About 50% of patients who suffer ACL injuries develop osteoarthritis within 10-15 years (15). An oral preventative would be convenient for patients who have suffered an ACL tear or meniscal injuries and are otherwise asymptomatic.

The C'-CEO formulation may not only modify the course of the disease directly, but also relieve pain symptoms and improve mobility. Results in studies with post-traumatic osteoarthritis mice makes the C'-CEO formulation potentially extremely valuable because pain relief and improved mobility are significant goals of clinical treatments. Uncontrolled pain is a primary reason why patients chose joint-replacement surgery (16).

The C'-CEO formulation may also be used to treat other forms of arthritis including rheumatoid arthritis. Inflammation, cartilage degradation and chronic pain are common hallmarks of all forms of arthritis including osteoarthritis and rheumatoid arthritis (17). The anti-inflammatory, anti-catabolic and analgesic actions of the C'-CEO formulation are likely to have beneficial effects on all forms of arthritic disease.

The components of the C'-CEO formulation were selected by molecular screening for the ability to stimulate production of a regulatory protein having a range of cartilage-maintaining (chondroprotective) properties. These include suppressing the expression of several tissue-degrading enzymes implicated in the pathophysiology of osteoarthritis. The components of the C'-CEO formulation are individual nutraceutical compounds that induce a chondroprotective transcriptional regulator CITED2 (Cbp/p300 Interacting Transactivator with ED-rich tail 2), a potential OA therapeutic target (29-32). These studies suggest that CITED2 not only modulates signal pathways related to chondrocyte homeostasis, but also protects cartilage integrity.

In addition, the components of the C'-CEO formulation were expressly chosen from a class of food products ("nutraceuticals") that are likely to be well tolerated over long periods of chronic treatment. Nutraceuticals, as food or diet supplements, are traditionally considered to provide medical or health benefits and to be potentially safe alternatives to standard pharmacologic therapies (18-27). The nutraceuticals proposed for osteoarthritis treatment are derived in some cases from traditional alternative medicine (28) or based on their general anti-inflammatory effects (18). Before the present study, the effectiveness of nutraceuticals in preventing or slowing osteoarthritis progression has not been well established (13).

The compounds that constitute the C'-CEO formulation are regarded as safe (GRAS) by the FDA. This is particularly important as osteoarthritis has become more prevalent in adults over 40 years and risk factors including joint injuries, obesity and diabetes may lead to disease development at even younger ages (14). Non-toxic nutraceuticals can be used safely in individual patients over the decades necessary for meaningful benefit (13).

REFERENCES

1. Lawrence, R. C., et al. Estimates of the prevalence of arthritis and other rheumatic conditions in the United States. Part II. *Arthritis Rheum* 58, 26-35 (2008).
2. Suri, P., Morgenroth, D. C. & Hunter, D. J. Epidemiology of osteoarthritis and associated comorbidities. *PM R* 4, S10-19 (2012).
3. Kotlarz, H., Gunnarsson, C. L., Fang, H. & Rizzo, J. A. Insurer and out-of-pocket costs of osteoarthritis in the US: evidence from national survey data. *Arthritis Rheum* 60, 3546-3553 (2009).
4. Loeser, R. F., Goldring, S. R., Scanzello, C. R. & Goldring, M. B. Osteoarthritis: a disease of the joint as an organ. *Arthritis Rheum* 64, 1697-1707 (2012).
5. Le Graverand-Gastineau, M. P. Disease modifying osteoarthritis drugs: facing development challenges and choosing molecular targets. *Curr Drug Targets* 11, 528-535 (2010).
6. Evans, C. H., Ghivizzani, S. C. & Robbins, P. D. Getting arthritis gene therapy into the clinic. *Nat Rev Rheumatol* 7, 244-249 (2011).
7. Heinegard, D. & Saxne, T. The role of the cartilage matrix in osteoarthritis. *Nat Rev Rheumatol* 7, 50-56 (2011).
8. Bruyere, O., et al. An algorithm recommendation for the management of knee osteoarthritis in Europe and internationally: A report from a task force of the European Society for Clinical and Economic Aspects of Osteoporosis and Osteoarthritis (ESCEO). *Seminars in arthritis and rheumatism* (2014).
9. Hashimoto, M., Nakasa, T., Hikata, T. & Asahara, H. Molecular network of cartilage homeostasis and osteoarthritis. *Med Res Rev* 28, 464-481 (2008).
10. Cheng, D. S. & Visco, C. J. Pharmaceutical therapy for osteoarthritis. *PM R* 4, S82-88 (2012).
11. O'Neil, C. K., Hanlon, J. T. & Marcum, Z. A. Adverse effects of analgesics commonly used by older adults with osteoarthritis: focus on non-opioid and opioid analgesics. *Am J Geriatr Pharmacother* 10, 331-342 (2012).
12. Van Manen, M. D., Nace, J. & Mont, M. A. Management of primary knee osteoarthritis and indications for total knee arthroplasty for general practitioners. *J Am Osteopath Assoc* 112, 709-715 (2012).
13. Leong, D. J., et al. Nutraceuticals: potential for chondroprotection and molecular targeting of osteoarthritis. *Int J Mot Sci* 14, 23063-23085 (2013).
14. Losina, E. & Katz, J. N. Total knee arthroplasty on the rise in younger patients: are we sure that past performance will guarantee future success? *Arthritis Rheum* 64, 339-341 (2012).
15. Wong, J. M., Khan, T., Jayadev, C. S., Khan, W. & Johnstone, D. Anterior cruciate ligament rupture and osteoarthritis progression. *The open orthopaedics journal* 6, 295-300 (2012).
16. Dieppe, P. A. & Lohmander, L. S. Pathogenesis and management of pain in osteoarthritis. *Lancet* 365, 965-973 (2005).
17. Goldring, M. B. & Marcu, K. B. Cartilage homeostasis in health and rheumatic diseases. *Arthritis Res Ther* 11, 224 (2009).
18. Akhtar, N. & Haqqi, T. M. Current nutraceuticals in the management of osteoarthritis: a review. *Ther Adv Musculoskelet Dis* 4, 181-207 (2012).
19. Henrotin, Y., Lambert, C., Couchourel, D., Ripoll, C. & Chiotelli, E. Nutraceuticals: do they represent a new era in the management of osteoarthritis?—a narrative review from the lessons taken with five products. *Osteoarthritis Cartilage* 19, 1-21 (2011).
20. Shen, C. L., et al. Dietary polyphenols and mechanisms of osteoarthritis. *J Nutr Biochem* 23, 1367-1377 (2012).
21. Mobasheri, A. Intersection of inflammation and herbal medicine in the treatment of osteoarthritis. *Curr Rheumatol Rep* 14, 604-616 (2012).

22. Lopez, H. L. Nutritional interventions to prevent and treat osteoarthritis. Part II: focus on micronutrients and supportive nutraceuticals. *PM R* 4, S155-168 (2012).
23. Lopez, H. L. Nutritional interventions to prevent and treat osteoarthritis. Part I: focus on fatty acids and macronutrients. *PM R* 4, S145-154 (2012).
24. Vandeweerd, J. M., et al. Systematic review of efficacy of nutraceuticals to alleviate clinical signs of osteoarthritis. *J Vet Intern Med* 26, 448-456 (2012).
25. Olsen, N. J. Nutraceuticals for the treatment of osteoarthritis. *Minerva Med* 102, 33-40 (2011).
26. Ernst, E. Herbal medicine in the treatment of rheumatic diseases. *Rheum Dis Clin North Am* 37, 95-102 (2011).
27. Rosenbaum, C. C., O'Mathuna, D. P., Chavez, M. & Shields, K. Antioxidants and antiinflammatory dietary supplements for osteoarthritis and rheumatoid arthritis. *Altern Ther Health Med* 16, 32-40 (2010).
28. Ameye, L. G. & Chee, W. S. Osteoarthritis and nutrition. From nutraceuticals to functional foods: a systematic review of the scientific evidence. *Arthritis Res Ther* 8, R127 (2006).
29. Leong, D. J., et al. The role of CITED2 in the pathogenesis of osteoarthritis. *ORS Transactions* (2012).
30. Leong, D. J., et al. The chondroprotective role of CITED2 in post-traumatic osteoarthritis. *Osteoarthr Cartilage* 21, 5304-5305 (2013).
31. Leong, D. J., et al. CITED2 is required for cartilage homeostasis: deletion of CITED2 in skeletally mature mice leads to osteoarthritis. *ORS Transactions* (2014).
32. Leong, D. J., et al. CITED2 suppresses senescence through p21: A new role in Chondroprotection. *ORS Transactions* (2013).
33. Glasson, S. S., Chambers, M. G., Van Den Berg, W. B. & Little, C. B. The OARSI histopathology initiative—recommendations for histological assessments of osteoarthritis in the mouse. *Osteoarthritis Cartilage* 18 Suppl 3, S17-23 (2010).
34. Chaplan, S. R., Bach, F. W., Pogrel, J. W., Chung, J. M. & Yaksh, T. L. Quantitative assessment of tactile allodynia in the rat paw. *J Neurosci Methods* 53, 55-63 (1994).
35. Leong, D., et al. Epigallocatechin-3-gallate (EGCG) inhibits HDAC7 in chondrocytes through CITED2. *ORS Transactions* 36, 1946 (2011).
36. Glasson S S, Blanchet T J, Morris E A: The surgical destabilization of the medial meniscus (DMM) model of osteoarthritis in the 129/SvEv mouse. *Osteoarthritis Cartilage* 2007, 15:1061-1069.
37. Nguyen D: Quantifying chromogen intensity in immunohistochemistry via reciprocal intensity. 2013.
38. Hanstein R, Zhao J B, Basak R, Smith D N, Zuckerman Y Y, Hanani M, Spray D C, Gulinello M: Focal Inflammation Causes Carbenoxolone-Sensitive Tactile Hypersensitivity in Mice. *The open pain journal* 2010, 3:123-133.
39. Bailey K R, Crawley J N: Anxiety-Related Behaviors in Mice. In *Methods of Behavior Analysis in Neuroscience.* 2nd edition. Edited by Buccafusco J J. Boca Raton (Fla.); 2009: *Frontiers in Neuroscience*].

What is claimed is:

1. A method of treating osteoarthritis in a subject in need thereof, comprising administering to the subject as active agents:

a therapeutically-effective amount of carvacrol;
a therapeutically-effective amount of curcumin;
a therapeutically-effective amount of epigallocatechin-3-gallate; and
a therapeutically-effective amount of oligomeric procyanidins, wherein the therapeutically-effective amounts of carvacrol, curcumin, epigallocatechin-3-gallate, and oligomeric procyanidins are selected to synergistically increase expression of Cbp/p300 interacting transactivator with ED-rich tail 2 (CITED2) in the subject, and wherein the carvacrol, the curcumin, the epigallocatechin-3-gallate, and the oligomeric procyanidins are present in a molar ratio of 1:1:100:50 or in a weight ratio of 10:10:1:10.

2. The method of claim 1, wherein the active agents are in a pharmaceutical formulation and the pharmaceutical formulation further comprises a pharmaceutically acceptable carrier.

3. The method of claim 1, wherein the carvacrol, the curcumin, the epigallocatechin-3-gallate, and the oligomeric procyanidins are present in the molar ratio of 1:1:100:50.

4. The method of claim 1, wherein the carvacrol, the curcumin, the epigallocatechin-3-gallate, and the oligomeric procyanidins are present in the weight ratio of 10:10:1:10.

5. The method of claim 1, wherein the administering is by injection.

6. The method of claim 1, wherein the administering is topical.

7. The method of claim 1, wherein the administering is oral.

8. The method of claim 1, wherein the administering reduces cartilage degradation associated with the osteoarthritis in the subject.

9. The method of claim 1, wherein the administering reduces inflammation associated with the osteoarthritis in the subject.

10. The method of claim 1, wherein the administering reduces pain symptoms associated with the osteoarthritis in the subject.

11. The method of claim 1, wherein the administering suppresses expression of a cartilage degradation enzyme in the subject.

12. The method of claim 1, wherein the administering suppresses expression of matrix metalloproteinase-1 (MMP-1) in the subject.

13. The method of claim 1, wherein the administering suppresses expression of matrix metalloproteinase-3 (MMP-3) in the subject.

14. The method of claim 1, wherein the administering suppresses expression of matrix metalloproteinase-13 (MMP-13) in the subject.

15. The method of claim 1, wherein the administering suppresses expression of ADAM metallopeptidase with thrombospondin type 1 motif 5 (ADAMTS5) in the subject.

16. The method of claim 1, wherein the administering suppresses expression of tumor necrosis factor-alpha (TNF-α) in the subject.

* * * * *